US00PP22650P2

(12) United States Plant Patent
Doherty

(10) Patent No.: US PP22,650 P2
(45) Date of Patent: Apr. 17, 2012

(54) ***LOPHOMYRTUS* PLANT NAMED 'MAGIC DRAGON'**

(50) Latin Name: *Lophomyrtus ralphii*
Varietal Denomination: Magic Dragon

(76) Inventor: Malachy F. Doherty, C. Waterford (IE)

( * ) Notice: Subject to any disclaimer, the term of this patent is extended or adjusted under 35 U.S.C. 154(b) by 2 days.

(21) Appl. No.: 12/924,463

(22) Filed: Sep. 28, 2010

(51) Int. Cl.
*A01H 5/00* (2006.01)

(52) U.S. Cl. ..... Plt./226

(58) Field of Classification Search ..... Plt./226
See application file for complete search history.

(56) References Cited

OTHER PUBLICATIONS fitzgerald-nurseries.com—excerpt depicting and describing *Lophomyrtus* 'Magic Dragon'.*

* cited by examiner

*Primary Examiner* — Howard Locker
(74) *Attorney, Agent, or Firm* — Penny J. Aguipre

(57) ABSTRACT

A new cultivar of *Lophomyrtus*, 'Magic Dragon', that is characterized by its variegated foliage with burgundy centers and creamy white to light pink margins, and its densely branched and broadly upright plant habit.

2 Drawing Sheets

Botanical classification: *Lophomyrtus ralphii*.
Variety denomination: 'Magic Dragon'.

BACKGROUND OF THE INVENTION

The present invention relates to a new and distinct cultivar of *Lophomyrtus ralphii* and will be referred to hereafter by its cultivar name, 'Magic Dragon'. 'Magic Dragon' is a new cultivar of shrub grown for use as an ornamental landscape and container plant.

The Inventor discovered the new cultivar, 'Magic Dragon', as a branch mutation of 'Red Dragon' (not patented) in a container in a nursery in Coolbunnia, Ireland in the August of 2004.

Asexual reproduction of the new cultivar was first accomplished by the Inventor using softwood stem cuttings in February of 2005 in Coolbunnia, Ireland. The characteristics of this cultivar have been determined to be stable and are reproduced true to type in successive generations.

SUMMARY OF THE INVENTION

The following traits have been repeatedly observed and represent the characteristics of the new cultivar as grown outdoors in a trial plot for five years in Coolbunnia, Ireland. These attributes in combination distinguish 'Magic Dragon' as a unique cultivar of *Lophomyrtus*.

1. 'Magic Dragon' exhibits variegated foliage with burgundy centers and creamy white to light pink margins.
2. 'Magic Dragon' exhibits a densely branched and broadly upright plant habit.

The parent plant, 'Red Dragon' differs from 'Magic Dragon' in having burgundy colored foliage that is non-variegated. 'Magic Dragon' can be most compared to the cultivars 'Little Star' (not patented). 'Little Star' is similar to 'Magic Dragon' in having variegated foliage with creamy white to pink margins, 'Little Star' differs from 'Magic Dragon' in being shorter in height and in having leaves that are more rounded in shape and that have dark green centers rather than burgundy centers.

BRIEF DESCRIPTION OF THE DRAWING

The accompanying colored photographs illustrate the overall appearance and distinct characteristics of a 4 year-old plants the new *Lophomyrtus* as grown outdoors in a 21-cm container in The Netherlands.

The photograph in FIG. 1 provides an overall view of the growth habit of 'Magic Dragon'.

Figure 1:
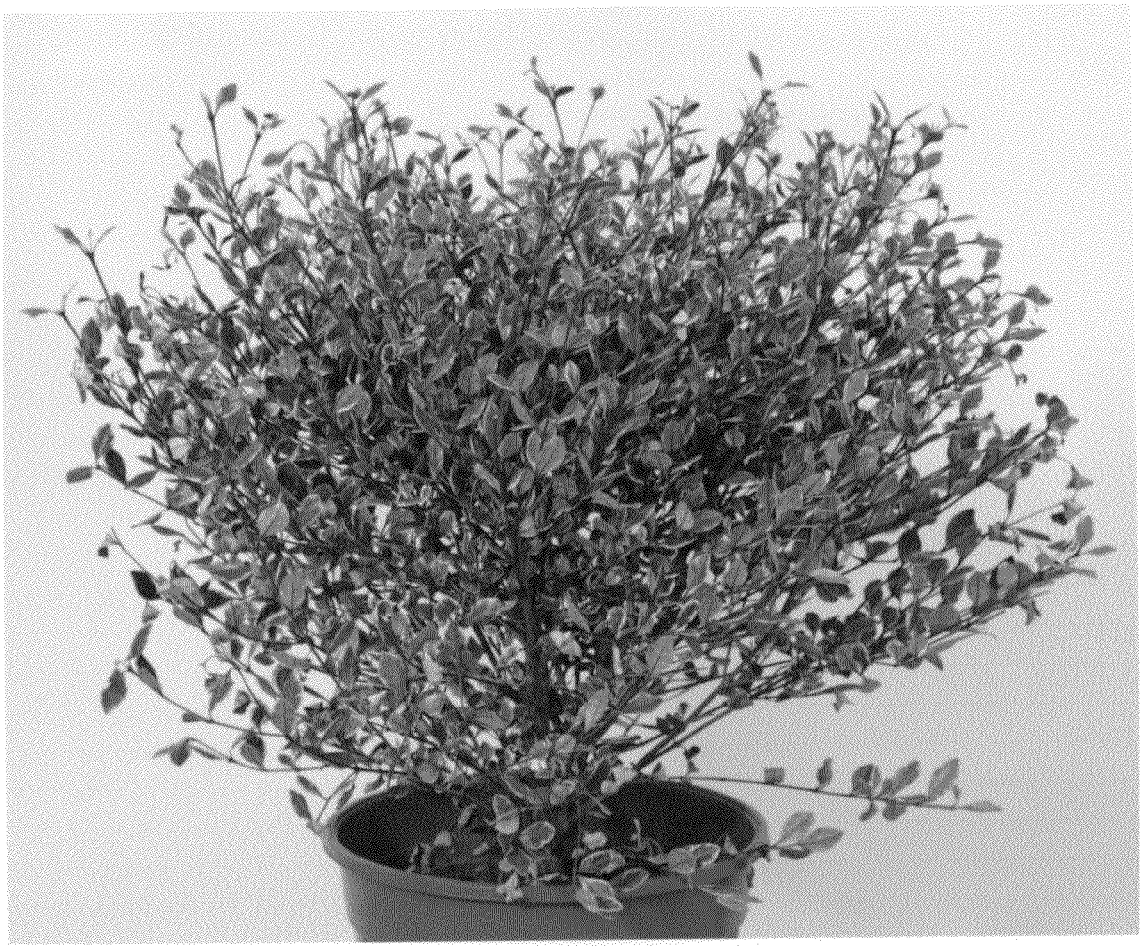
Figure 2:
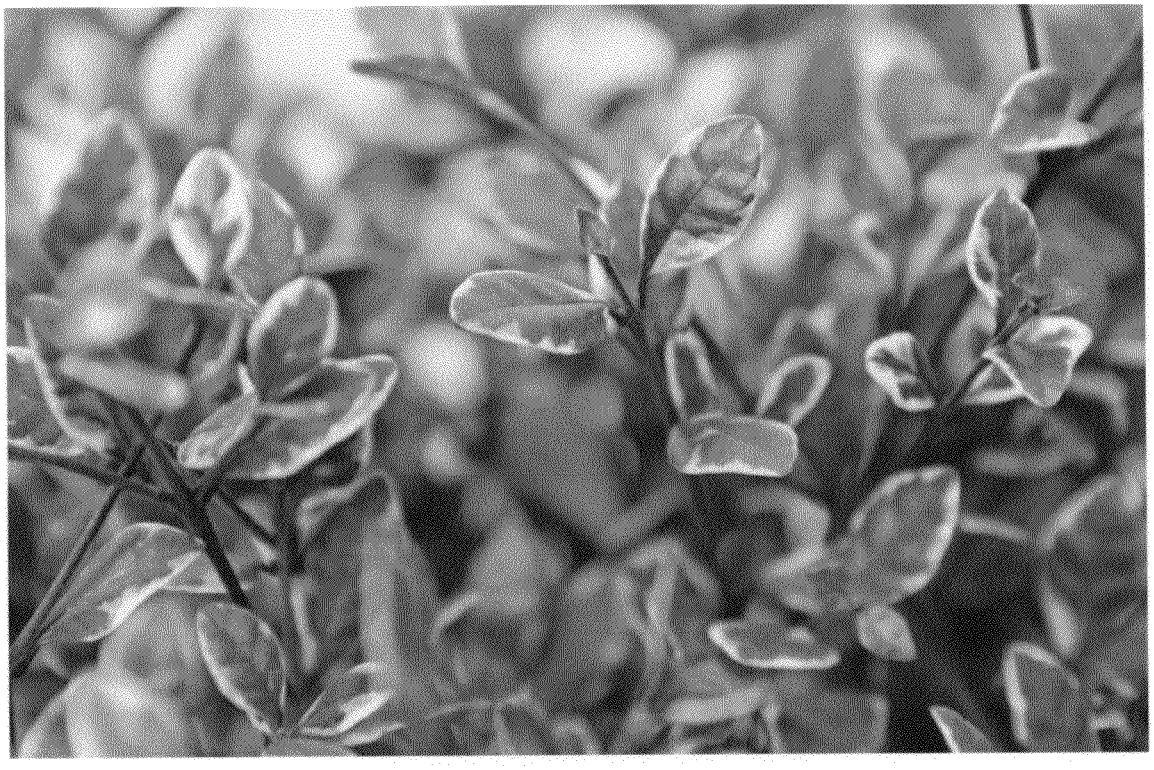

The photograph in FIG. 2 provides a close-up view of the foliage of 'Magic Dragon'. The colors in the photograph may differ slightly from the color values cited in the detailed botanical description, which accurately describe the colors of the new *Lophomyrtus*.

DETAILED BOTANICAL DESCRIPTION

The following is a detailed description of 4 year-old plants of the new cultivar as grown outdoors in 21-cm containers in Boskoop, The Netherlands. Plants were grown under average day temperatures of 14° C. to 32° C. and average night temperature of 5° C. to 18° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Blooms have not been observed to date on the plants available for data collection.

*Plant type*.—Evergreen shrub.

*Plant habit*.—Densely branched, broadly upright.

*Plant size*.—Reaches about 42 cm in height and 48 cm in spread in a 21-cm container, reaches about 1.6 m in height and 1.2 m in spread when grown in the landscape.

*Hardiness*.—At least in U.S.D.A. Zones 8b to 9.

*Environmental stress*.—Tolerant to wind and rain.

*Diseases and pests*.—No susceptibility or resistance to diseases or pests has been observed.

*Root description*.—Fibrous, moderately dense.

Growth and propagation:

*Propagation*.—Softwood stem cuttings.

*Root initiation*.—An average of 4 weeks at air temperatures of 18° to 20° C. during summer.

*Root development*.—An average of 3 months at air temperatures of 18° to 20° C. to finish a young plant during summer.

*Growth rate*.—Moderate.

Stem description:

*Shape*.—Rounded.

*Stem color*.—New and mature growth; 200C with nodes 183A.

*Stem size*.—An average of 16.9 cm in length and 2 mm in diameter.

*Stem surface*.—New growth; slightly glossy and covered with short adpressed hairs (about 0.2 mm in length and close to 156D in color), mature wood is dull and glabrous.

*Stem strength*.—Strong.

*Branching*.—Basal branching, an average of 240 lateral branches.

*Internode length*.—An average of 3.2 cm.

Foliage description:

*Leaf shape*.—Elliptic to obovate.

*Leaf division*.—Simple.

*Leaf base*.—Attenuate.

*Leaf apex*.—Broadly acute to obtuse.

*Leaf fragrance*.—None.

*Leaf venation*.—Pinnate, color upper and lower surface N186C to 187A.

*Leaf margins*.—Entire, slightly undulate.

*Leaf arrangement*.—Opposite.

*Leaf attachment*.—Petiolate.

*Leaf surface*.—Upper and lower surface; glossy and smooth.

*Leaf size*.—An average of 2 cm in length and 1 cm in width.

*Leaf color*.—Newly expanded leaves upper and lower surface; centers 147A with margins 156C to 156D to 196B to 196C with very outer edge 182A to 182B, mature leaves upper surface; centers 200A with a tinge of a color darker than 147A with margins 155A to 198B to 198D, mature leaves lower surface; centers a color between N77D and 183D and slightly darker with margins 182A.

*Petioles*.—About 5 mm in length and 1 mm in width, N186C in color, glabrous surface.

*Stipules*.—None.

*Durability to stresses*.—High.

Inflorescence description: No flowers have been observed to date on plants available for data collection.

It is claimed:

1. A new and distinct cultivar of *Lophomyrtus* plant named 'Magic Dragon' as herein illustrated and described.

* * * * *